United States Patent [19]

Fair

[11] Patent Number: 4,671,254

[45] Date of Patent: Jun. 9, 1987

[54] NON-SURGICAL METHOD FOR SUPPRESSION OF TUMOR GROWTH

[75] Inventor: William R. Fair, New York, N.Y.

[73] Assignee: Memorial Hospital for Cancer and Allied Diseases, New York, N.Y.

[21] Appl. No.: 708,438

[22] Filed: Mar. 1, 1985

[51] Int. Cl.$^4$ ............................................. A61B 17/00
[52] U.S. Cl. ................................................... 128/1 R
[58] Field of Search .............. 128/24 A, 24 R, 303 R, 128/303.1, 328, 804, 1 R

[56] References Cited

U.S. PATENT DOCUMENTS 4,425,115  1/1984  Wuchinich ...................... 128/303 R
4,526,168  7/1985  Hassler et al. ...................... 128/328

OTHER PUBLICATIONS

Wells, P. N. T., "Ultrasonics in Clinical Diagnosis", Churchill Livingstone, London & N.Y., 1977, pp. 173-180.

Anderson, W. A. D., "Synopsis of Pathology", C. V. Mosby Co., St. Louis, Mo., 1972, pp. 52-55.

Chaussy, C. H. et al., "Extracorporeal Shock Wave Lithotripsy", Karger Publ., N.Y., 1982, pp. 1-112.

Primary Examiner—Kyle L. Howell
Assistant Examiner—Francis J. Jaworski
Attorney, Agent, or Firm—Cooper, Dunham, Griffin & Moran

[57] ABSTRACT

This invention relates to a method for the non-surgical treatment of tumors. The method of this invention involves the use of shock waves to effect subcellular destruction of tumor cells, to alter their tumorigenic potential, and to suppress tumor growth.

16 Claims, 3 Drawing Figures

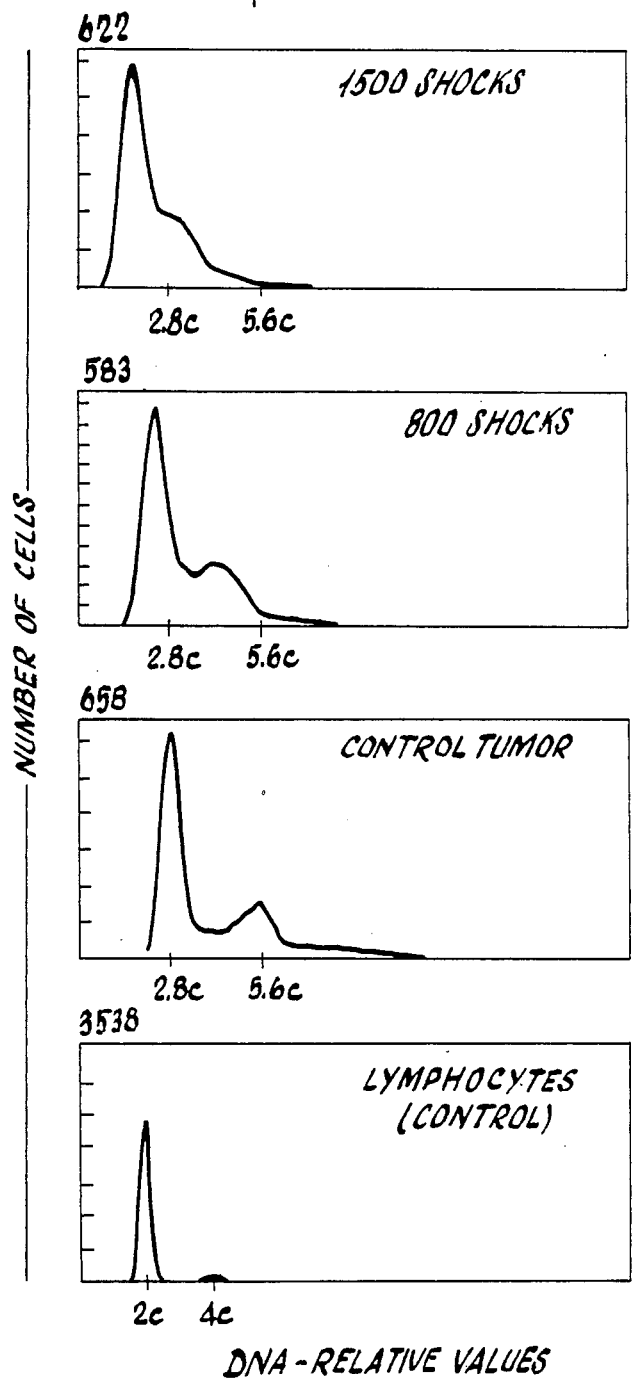

NON-SURGICAL METHOD FOR SUPPRESSION OF TUMOR GROWTH

TECHNICAL FIELD

This invention relates to a non-surgical method for treating tumors and suppressing tumor growth. More specifically, this invention relates to a method for the treatment of tumor-bearing animals, including humans, involving exposure of a tumor to high energy shock waves ("HESW") to alter the tumorigenic potential of tumor cells and suppress tumor growth. The method of the invention provides a safe and effective alternative to surgical techniques for the treatment of tumors.

BACKGROUND OF THE INVENTION

Surgical removal of tumors has been one of the conventional treatments for cancer. Such treatment is attended by the high degree of pain and disability, and increased susceptibility to infection which accompanies any surgical procedure. In addition, scarring of tissue inevitably occurs. Due to the substantial disadvantages of surgery, there continues to exist a need for the non-invasive treatment of tumors.

Non-invasive techniques hae been employed in various types of medical protocols. For example, U.S. Pat. Nos. 3,237,623, 3,735,755, and 4,441,486 refer to the use of ultrasound waves to destroy various tissues or cells, and U.S. Pat. No. 4,315,514 refers to the use of selected frequencies of ultrasound to destroy tumor cells. However, because long exposure to ultrasound results in cellular (thermal) degradation, the use of ultrasound waves for the suppression of tumor cells is not favored.

Shock wave technology is currently being used for the non-invasive destruction of human renal and ureteral calcified deposits ("extracorporeal shock wave lithotripsy"). C. Chaussy et al., *Lancet*, 1:1265 (1980); C. Chaussy et al., *J. Urology*, 127:417 (1982); E. Schmiedt, C. Chaussy, *Urol Int* 39:193 (1984). In this technique, HESW are focused by a brass semi-ellipse of high acoustical impedance to a second focal point ($F_2$).

In contrast to an ultrasonic wave, which consists of sinusoidal wave form, a shock wave consists of a single positive pressure spike with very steep onset and gradual relaxation. While ultrasound can generate pressure waves of approximately 0.1 bar, shock waves can generate pressure amplitudes of up to 1000 bar or more.

Ultrasound is capable of creating a mechanical shock, which is felt at a distance of a few microns. If the ultrasonic wave traveling through a liquid is high enough in amplitude, a microscopic bubble or cavity is produed. This phenomenon, known as cavitation, can produce bubbles of a resonant size which collapse violently to produce high local pressure charges of up to 20,000 atmospheres. For example, at 20 KHz, the resonant bubble size is about 150 microns. H. Alliger, "Ultrasonic Disruption," *American Laboratory*, (1975).

Shock waves have a greater depth of penetration than ultrasonic waves. Because of this feature, focused shock waves have been used to break up urinary concrements, as discussed briefly above. In those procedures, patients are submergeed in a water-bath and the urinary stone is visualized by the use of two dimensional fluoroscopy. The generated shock wave is propagated through both water and tissue at nearly identical velocities as a result of similar acoustical imedance. However, the target stone, with its high acoustical impedance, is said to absorb and reflect a significant portion of the shock wave. By repeated shock wave exposures in the range of 1000 to 2000 shocks, non-invasive stone disintegration is said to be achieved. The multiple small fragments produced are then said to pass through the intact urinary tract and be excreted in the urine.

Similary, U.S. Pat. No. 3,942,531 refers to the use of shock waves to destroy calcified deposits in the urinary tract. The '531 patent refers to an elliptical container which is applied directly on the skin of the body in an airtight manner. This technique relies on the shock waves' selective attack on the calcified stone, which is said to leave the surrounding tissue intact.

To date, however, there has been no disclosure or investigation of the use of shock waves to destroy or eliminate tissue growth abnormalities such as tumors. On the contrary, clinical use of shock waves, to destory urinary concrements, has been said to be based on the premise that shock waves, meeting with the substantially greater acoustical impedance of the stone, pulverize the stone while "other parts of the body are not affected thereby" ('531 patent, Col. 1, lines 61–63).

SUMMARY OF THE INVENTION

The present invention provides a nonsurgical method of treating tumors by altering the tumorigenic potential of tumor cells and suppressing tumor growth. As will be appreciated from the disclosure to follow, this invention advantageously provides a method which has none of the above-stated disadvantages of ultrasound techniques. The method of this invention comprises a process for the treatment of tumor-bearing animals including humans, by exposue of a tumor to HESW, which results in a significant delay in tumor growth. More particularly, the method of this invention comprises the steps of locating the tumor in the body of the patient and generating a high energy shock wave towards a point that coincides with the position of the tumor.

The present invention has none of the disadvantages associated with the surgical treatment of tumors. HESW treatment would thus minimize the pain, morbidity, mortality and convalescence expenses associated with conventional surgical techniques.

The present invention also has none of the disadvantages of ultrasonic wave medical treatment and its resultant thermal degradation of tissue. Rather, the method herein disclosed recognizes and demonstrates that soft tumor tissue can be affected by shock waves in order to suppress tumor growth—which is unexpected in view of the afore-quoted belief that shock waves leave all soft tissue "substantially intact". Thus, HESW therapy is a desirable technique, which offers a safe and effective alternative to surgical techniques for the removal of tumors.

BRIEF DESCRIPTION OF THE DRAWINGS

FIG. 2 (comprising FIGS. 2A, 2B, 2C, and 2D) is a graphic representation of flow cytometry for total DNA content, plotting the number of cells of normal human lymphocytes, control R3327AT-3, and cells exposed to 800 and 1500 HESW, respectively, against relative DNA values.

DESCRIPTION OF THE PREFERRED EMBODIMENTS

Figure 1A:
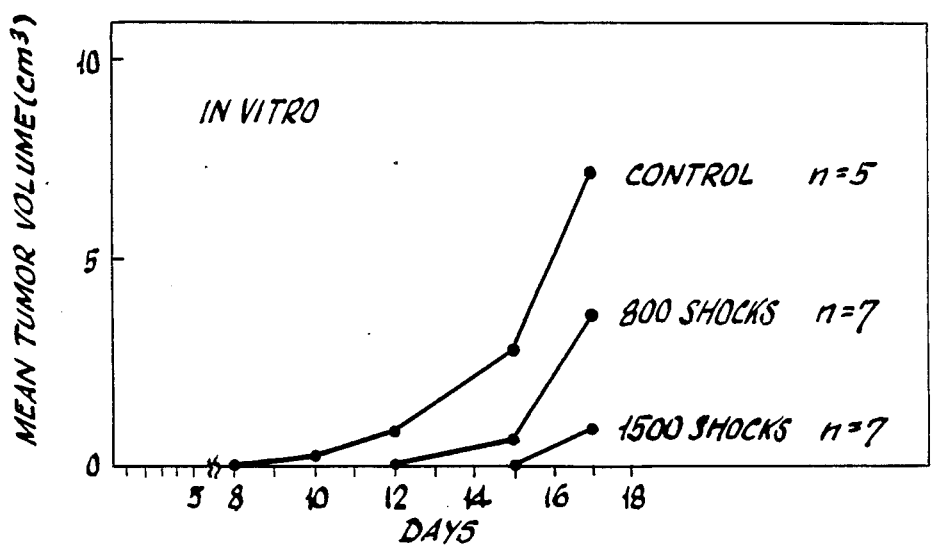
FIG. 1A is a graphic representation of the in vitro tumorigenic potential of R3327AT-3 rat prostatic cancer cells after exposure to HESW, plotting mean tumor volume ($cm^3$) against days.

According to the method of this invention high energy shock waves are used for the non-surgical treatment of tumors. This method advantageously provides a non-invasive method for the treatment of tumor-bearing human patients, which apparently disrupts tumor cells on a subcellular level. It has been found that although tumors are composed of relatively "soft" tissue, the high energy shock wave can selectively disrupt tumor cells, and leave the normal cells of the surrounding tissue largely intact. The term "tumor", as used herein, relates to tissue growth abnormalities which may form a swelling or a group of malignant or benign, atypical or abnormal cells which appear within or upon the body of the animal to be treated. While not wishing to be bound by theory, it is believed that the tumor cells are selectively affected by the shock wave because of their relative density.

While tumors are actually composed of a heterogeneous population of cells, tumor cells frequently possess a greater complement of DNA, i.e., they have more DNA than the normal (2n) complement. Those tumor cells which possess a greater complement of DNA have a greater density than normal cells. FIG. 2, represents some tumor cells with the normal "2n" complement of DNA (the first peak) and some cells with a larger than normal complement (second peak). After treatment with HESW the second peak merges with the first, indicating that normal cells are unaffected and only the abnormal, denser cells are selectively killed.

According to one embodiment of this invention, the method of treatment begins by first localizing the tumor tissue. This can be accomplished by any conventional means, including ultrasound, visual means, fluoroscopy, nuclear magnetic resonance, CT scanning, or any other method suitable for localizing tumor growth.

The patient is anesthetized by any conventional means, and then placed in a tub, preferably filled with de-gassed water to prevent bubble formation which can interfere with the transmission of shock waves. If necessary, the patient can be held in position with restraining straps.

Next, the high energy shock waves are generated outside the body. A shock wave may be generated in water to enter into the patients biological soft tissue in a largely unimpeded manner. Alternatively, the shock wave may be generated at a point directly against the patient's body, so that the shock wave would pass through the body to reach the tumor positioned at the second focal point.

The HESW utilized in this invention may be generated by any suitable means. For example, the HESW may be generated by underwater sparks whereby an underwater electrode discharges stored electrical energy in approximately 0.5 microseconds. Once created, the spark causes vaporization of water, which generates a spherically propagated pressure wave in the surrounding liquid. Alternatively, the shock waves may be generated by laser, whereby, the heat generated by laser light causes vaporization of water in an explosive manner. In another embodiment, the shock waves may be created by chemical explosion. Regardless of the means selected to generate the shock waves, the frequency of the shock waves should be in the range of about 100,000 hz to 100 mhz, preferably between about 500,000 hz and 50 mhz.

According to one embodiment of the invention, shock waves are generated from underwater sparks using the Dornier Lithotripter machine. This machine has been used successfully in the treatment of urinary concrements. FDA approval of its use in the treatment of such calcified deposits was granted in December 1984, after the Lithotripter had been widely used in the United States and Europe.

In this embodiment of the invention, the shock waves are focused to reach the target tumor tissue. A reflector, which has the shape of an upward-opened semiellipsoid, is incorporated into the floor of the Dornier tub. Electrodes protrude horizontally into the ellipsoid reflector in such a way that the discharge occurs at the lower focal point of the ellipsoid. The waves are focused by placing the electrode at one focal point of the symmetrical ellipsoidal cavity (F1). The shock waves are reflected by the walls of the ellipsoid reflector and concentrated in the second focal point (F2), where the tumor is located.

Energy for the discharge is stored in the pulse current generator. The electrode is connected mechanically and electrically to the pulse current generator. Ignition of the underwater spark is controlled by an electrocardiographic triggering unit that monitors the patient's heart rate.

The tumor is localized via the focusing system of the Lithotripter. This system consists of a two-axis X-ray system which is permanently secured to the Lithotripter mounting and radiates horizontally at an angle of 55° through the windows in the floor of the tub, so that the X-ray axes intersect at the focal point F2 of the reflector; the corresponding image intensifiers are mounted on a movable pivoting arm. When the patient has been lowered into the tub, the image intensifiers are manually placed into the radiation path of the X-ray tubes and then are moved by motor along the radiation path as close as possible to the patient. An automatic cut-off prevents further movement of the image intensifiers when contact is made with the patient. The fluoroscopic (X-ray) picture is transferred to two television display units on which, with the aid of cross hairs, the exact position of the tumor in relation to the focal point (F2) may be determined.

In the preferred method of the present invention, the patient is positiond so that the tumor is in line with the second focal point of the reflector. The patient may be placed on an overhead support, which permits the optimum application of the shock waves. The movement of the patient support in three coordinates is achieved by a positioning unit, which is guided from a crane runway installed on the ceiling of the room. The initial movement of the patient support to the position above the bath is carried out manually. The positioning procedures—the vertical, longitudinal, and lateral movements—are controlled from a control cabinet by an hydraulic drive unit.

The patient is thus placed in the bathtub of stainless steel, constructed so that a tumor in any position on the body can be localized and positioned in the upper focal point of the reflector. The shock wave electrode, the elliptical reflector and the windows required by the passage of X-rays should be located in the floor of the tub. The water should be temperature controlled and de-gassed to remove dissolved oxygen, carbon dioxide and nitrogen.

Abdominal organs can tolerate pressure waves in the 2.5–3 kilobar range. Lungs, however, must be protected from the shock wave by styrofoam or a similar material to avoid significant damage. The characteristics of styrofoam which make it a desirable material to block shock waves are described in C. Chaussy, et al. *Extracorporeal Shock Wave Lithotripsy*, page 35. For the treatment of a tumor located in the lung, a hole may be cut in a protective vest, positioned over the portion of the lung containing the tumor.

The patient should be scheduled to receive a series of fractionated HESW treatments. Each session should involve administration of between 500 and 6000 shocks, preferably 800 to 3000 shocks per treatment. The method of this invention may be used in conjunction with conventional cancer treatment such as chemotherapy, immunotherapy or radiation. It is believed that one of the benefical effects of HESW treatments in conjunction with such conventional cancer treatment is the possible reduction in the amount of alternative treatment needed.

EXAMPLES

The following examples demonstrate the method of HESW treatment of tumor cells according to the invention. These examples are set forth for the purpose of illustration only and are not to be construed as limiting the scope of the invention in any manner.

Example 1

This example demonstrates the effects of HESW on Dunning R3327AT-3 rat prostatic carcinoma cells in vitro. R3327AT-3 cells were provided to me by Dr. J. T. Issacs of the Brady Urological Institute, Johns Hopkins University School of Medicine, Baltimore, Md. R3327AT-3 rat prostatic carcinoma is a hormone insensitive, anaplastic prostate cancer. J. T. Issacs et al., *Cancer Res.* 38:4353 (1978). Histologically, it appears as sheets of anaplastic cells without acini or glandular elements. There is no evidence of secretory activity. The doubling time is between 1 day in vitro and 1.7 days in vivo. When 100,000 viable cells are injected into rats, the time to achieve a tumor volume of 1 cm$^3$ is approximately 12 days with eventual large local growth and lymphatic and pulmonary metastases.

I maintained the Dunning R3327AT-3 cells in standard tissue culture at 37° C. in RPMI 1640 supplemented with 10% fetal calf serum, 1% L-glutamine, 1% non essential amino acids, 1 ng/ml dexamethasone, 100 $\mu$/ml of penicillin and 100 mcg/ml of streptomycin. I grew the cells to subconfluence and created a single cell suspension by mechanical dispersion. I then transferred 1.5 ml aliquots with concentrations of $1 \times 10^6$ cells/ml to 5 ml polypropylene test tubes (Falcon, Cockeysville MD). I then prepared a separate group of experimental cells and a separate control group of cells, which were treated identically except for the HESW treatment.

I next placed my experimental cell suspension of R3327AT-3 cells in a test tube holder designed to fit a base portion over the brass ellipse in the Dornier Lithotripter and hold a test tube in the second focal point of the Dornier Lithotripter (supplied by Urotech, Ltd., Houston, Tex.).

I then subjected the cells to HESW. I set the operating voltage at 18 kilo volts so as to deliver 100 shocks/min to the cells which were to receive a total of 800 and 1500 HESW. The waterbath temperature was kept constant at 37° C. and the water level was always above the cell suspension within the test tube. I placed the unshocked control cells peripherally in the water bath, but out of the focus of the HESW.

I determined the percentage of viable cells immediately after exposure to HESW and again at 24 hours in cells returned to tissue culture. Table 1 indicates my observations: immediately after HESW, there was a moderate decrease in viability of the cells, as determined by trypan blue exclusion.

I next performed a clonogenic assay by plating five thousand viable cells in triplicate and incubating them at 37° C. for six days, according to the method of B. R. Rao et al., *Cancer Res.*, 38:4431 (1978). After methanol fixation and hematoxylin staining, I counted the colonies which consisted of greater than 50 cells and expressed my results in colony forming units/5000 cells plated.

I observed that after 24 hours of incubation following HESW treatment, the viability of the treated cells returned to the level of the control cells. This represents the death or repair of sublethally damaged cells. I also observed a marked decrease in the ability of the treated cells to form colonies after HESW exposure (Table 1). The percentage decrease of cells capable of colony formation varied with the number of HESW delivered. These results indicate that HESW profoundly influences colony formation at shock levels which are not necessarily capable of causing immediate cell death.

TABLE 1

HIGH ENERGY SHOCK WAVES: EFFECT ON VIABILITY PERCENTAGE AND CLONOGENIC POTENTIAL OF R-3327AT-3 PROSTATIC CARCINOMA IN VITRO

| Time: | % cells viable | | Number of clonogenic survivors | % of control |
|---|---|---|---|---|
| | 0 hours | 24 hours | | |
| CONTROL | 97% | 95% | 245 ± 11 | (100%) |
| 800 SHOCKS | 88% | 96% | 72 ± 17 | (29%) |
| 1500 SHOCKS | 75% | 100% | 12 ± 02 | (5%) |

I subjected samples of R3327AT-3 cells to flow cytometric determination on DNA content following HESW exposure (FIG. 2). The fluorescent dye used was acridine orange, according to the method of F. Traganos et al., *J. Histochem Cytochem* 25:46 (1977). The results demonstrated a selective loss of the cells containing twice the normal complement of DNA (G2M polulation of cells) which corresponded to an increase in shocks administered. Cells maintained in tissue culture for 48 hours showed a reversion to control DNA distribution.

Next, I exposed 100,000 R3327AT-3 cells in 0.5 cc of media to HESW, and then injected them into the right anterior thigh of male Copenhagen rats weighing 150–200 grams. When the tumors became palpable, I measured them and calculated mean tumor volumes using the formula $L \times W \times H \times 0.523$, according to the method of J. K. Smolev et al., *Cancer Treat Rep.* 61:273 (1977).

In those rats receiving cells exposed to 800 and 1500 HESW, there was a pronounced delay in the time for the mean tumor volume to achieve 1 cm$^3$ (FIG. 1a). The time for the tumor to reach a mean volume of 1 cm$^3$ was 12 days for control rats receiving control cells and 15 and 17 days for rats receiving 800 and 1500 shocked cells, respectively. At 17 days the mean tumor volume of the rats receiving cells exposed to 1500 shocks was 1.00 cm$^3$, whereas the control tumor volume was 7.92 cm$^3$ (p=0.002). Therefore, a growth delay equal to a decrease tumor volume of 87% was achieved. This correlates with the 95% decrease (compare Table 1) which I observed with the in vitro clonogenic assay.

The in vivo effect of HESW was manifest by a 5-day delay in tumor growth (see Table 2). These results demonstrate that HESW not only suppresses tumor clonogenic capacity but also delays the rate of subsequent tumor development in rats.

TABLE 2

TUMOR PRODUCING POTENTIAL OF HESW TREATED R3327AT-3 CELLS

|  | DAYS TO 1 cm$^3$ | TUMOR VOLUME AT DAY 17 17 days in cm$^3$ |
|---|---|---|
| CONTROL | 12 | 7.92 ± 1.77 |
| 800 SHOCKS | 15 | 3.93 ± 0.83 |
| 1500 SHOCKS | 17 | 1.00 ± 0.23 | control vs. 800 (p + 0.079)
control vs. 1500 (p = 0.002)
800 vs. 1500 (p = 0.0092)

Example 2

This example demonstrates the effect of HESW on Dunning R3327AT-3 rat prostatic carcinoma cells in vivo. Ten rats with small palpable tumors (largest volume dimension 0.25 cm$^3$) in the anterior thigh were exposed to shocks targeted at the tumor using fluroscopic control. I placed the rats under ketamine anesthesia (8.0 mg/kg) and then placed them into a holder designed to tie the rats to a plastic platform.

Figure 1B:
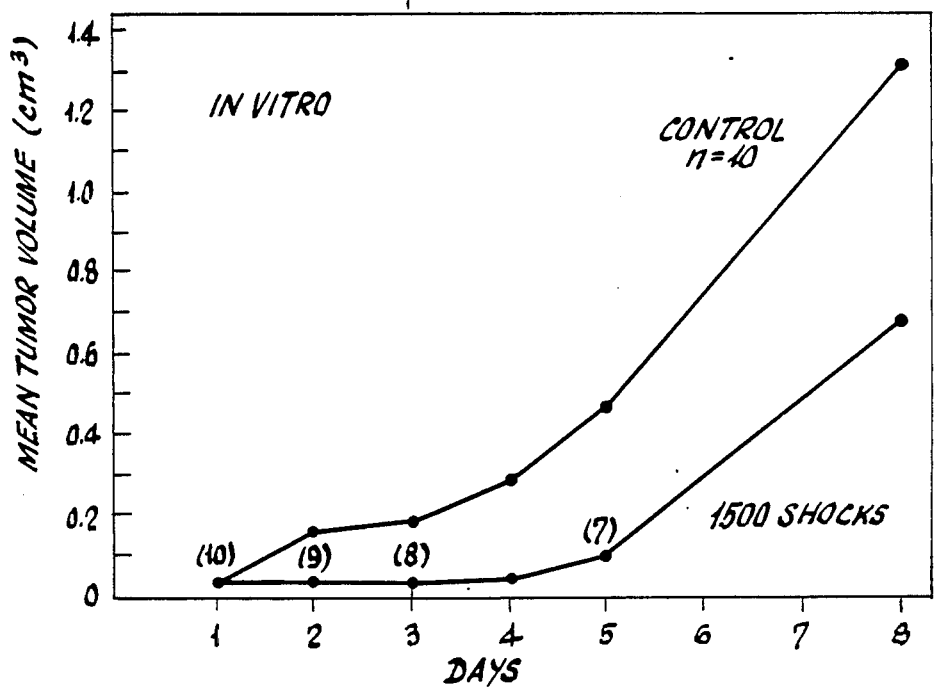
FIG. 1B is a graphic representation of in vivo effect of one treatment of HESW on R3327AT-3 tumor nodules, plotting tumor volume versus time.

With fluoroscopic guidance, using the Dornier machine, I maneuvered the tumors into the second focus of the HESW. 1500 HESW were delivered with operating voltage set at 18 kv and at a rate of 100 shocks/min (FIG. 1b). Ten tumor bearing rats treated similarly to those receiving the HESW but not subjected to HESW, served as my controls.

As a result of the HESW treatment, there was a retardation in growth rate during the first week after treatment (p>0.05). No rats died or suffered any ill-effects as a result of the HESW treatment and no control rats died during this period. One treated rat died of anesthetic complication on day 1, a second of small bowel obstruction on day 3, and a third of apparent cannibalism on day 4.

Tumors in the right anterior thigh of rats (largest volume dimension 1 cm$^3$) were subjected directly to 600 HESW and samples were obtained for light microscopy and transmission electron microscopy. After hematoxylin and eosin staining, I examined sections by light microscopy. There was no evidence of histologic damage after HESW, apart from hemorrhage surrounding the tumor, which had no detrimental effect on the animals.

However, transmission electron microscopy (1% glutaraldehyde fixation; 6,600 magnification) demonstrated progressive ultrastructural evidence of nuclear and cytoplasmic damage after HESW exposure. There was marked nuclear disruption with nuclei present in the cytoplasm. In addition, autolytic digestion granules were in the cytoplasm, and the mitochondria were damaged. The damage was most marked two days after HESW exposure.

Similar ultrastructural damage was not observed in control rats with tumors exposed to HESW. Rat prostatic carcinoma R3327AT-3 cells from control rats which had not been exposed to 600 HESW, had intact tumor cells, and tumor matrix, normal unclear morphology with the cytoplasmic organ cells intact.

Example 3

This example demonstrates the effect of HESW on a melanoma line. I followed a process similar to that described in Example 1, using the human melanoma line, SK-Mel-28. The human melanoma line was obtained through the courtesy of Dr. Lloyd Old's laboratory of Memorial Sloan Kettering Cancer Center, 1275 York Avenue, N.Y.C., N.Y. 10021. My experiments revealed an increase in sensitivity to HESW as compared to R3327AT-3, treated above in Examples 1 and 2.

I subjected the melanoma cells to 400 shocks, and observed that viability was decreased to 50%. After administering 800 shocks, viability was decreased to 5%. Colony formation was reduced to 5% of control by 400 shocks. This demonstrates a spectrum of susceptibility of cells to HESW.

While I have herein presented a number of embodiments of this invention, it is apparent that my basic construction can be altered to provide other embodiments which utilize the process of this invention. Therefore, it will be appreciated that the scope of this invention is to be defined by the claims appended hereto rather than by the specific embodiments which have been presented hereinbefore by way of example.

I claim:

1. A method for treating a tumor comprising tumor cells in vivo in the body of an animal, said method comprising the steps of exposing said tumor cells in vivo to a shock wave.

2. The method according to claim 1, wherein the body is immersed in a medium which is capable of propagating the shock wave.

3. The method according to claim 2, wherein the medium is liquid.

4. The method according to claim 1, wherein the tumor is located by a procedure selected from the group consisting of visual inspection, fluoroscopy, ultrasound, nuclear magnetic resonance, and CT scanning.

5. The method according to claim 1, wherein the shock wave is generated by a means selected from the group consisting of spark discharge means, laser, and means for producing a chemical explosion.

6. The method according to claim 1, wherein the shock wave is focused to coincide with the location of the tumor.

7. The method according to claim 1, wherein the animal is a human.

8. The method according to claim 1, wherein more than one tumor in the body is concurrently treated.

9. The method according to claim 1, wherein the frequency of the shock wave is within a range from about 100,000 hz to about 100 mhz.

10. The method according to claim 1, wherein the frequency of the shock wave is within a range from about 500,000 hz to about 50 mhz.

11. The method according to claim 1, further comprising exposing the tumor to a series of shock waves.

12. The method according to claim 11, wherein the number of shock waves administered per treatment is from about 500 to about 6000.

13. The method according to claim 11, wherein the number of shock waves administered per treatment is from about 800 to about 3000.

14. The method according to claim 1, further comprising the steps of protecting tissue surrounding the tumor by placing on said tissue, material capable of deflecting said shock waves.

15. A method according to claim 14, wherein said material is styrofoam.

16. The method according to claim 1, in combination with a cancer treatment selected from the group consisting of chemotherapy, immunotherapy, and radiation therapy.

* * * * *